United States Patent [19]

Grigg et al.

[11] 4,225,588

[45] Sep. 30, 1980

[54] ANTIBIOTIC MIXTURES

[75] Inventors: Geoffrey W. Grigg, Lane Cove; Wolfgang H. F. Sasse, Malvern East, both of Australia

[73] Assignee: Commonwealth Scientific & Industrial Research Organization, Campbell, Australia

[21] Appl. No.: 964,197

[22] Filed: Nov. 28, 1978

Related U.S. Application Data

[62] Division of Ser. No. 897,021, Apr. 17, 1978.

[30] Foreign Application Priority Data

Apr. 21, 1977 [AU] Australia .............................. PC9844

[51] Int. Cl.$^2$ ..................... A61K 37/02; C07C 103/52
[52] U.S. Cl. .............................. 424/177; 260/112.5 R
[58] Field of Search .................. 260/112.5 R; 424/177

[56] References Cited

U.S. PATENT DOCUMENTS 3,886,134   5/1975   Sipos et al. .................... 260/112.5 R Primary Examiner—Delbert R. Phillips
Attorney, Agent, or Firm—Dennis P. Clarke

[57] ABSTRACT

The use of various polycyclic nitrogen-containing compounds, such as triphenylmethane dyes to potentiate the bioactivity of antibiotics of the phleomycin series.

7 Claims, 4 Drawing Figures

PHLEOMYCIN

BLEOMYCIN

A

B

C

D

Where X is   CH;   CH$_2$;   N;   NH; O; S

Y is    CH;   CH$_2$;   N;   O; S

TYPE 2

A    c.f TYPE IA (X ≠ O or S)

B

C

} c.f TYPE IB

D    c.f TYPE IC

TYPE 3

ANTIBIOTIC MIXTURES

This is a division of application Ser. No. 897,021, filed Apr. 17, 1978.

PATENTABILITY STATEMENT

The specification acknowledges that it is known that phleomycins may be potentiated by administration in association with various types of compounds. However, we know of no prior publication whatsoever which would indicate the suitability of compounds of the present application for this purpose. U.S. patent applications corresponding to copending Australian Application No. 84888/75 referred to at page 2, line 7 are Ser. Nos. 613,879 and 828,875.

This invention concerns compounds able to potentiate the antibiotics, phleomycin and bleomycin.

Figure 1:
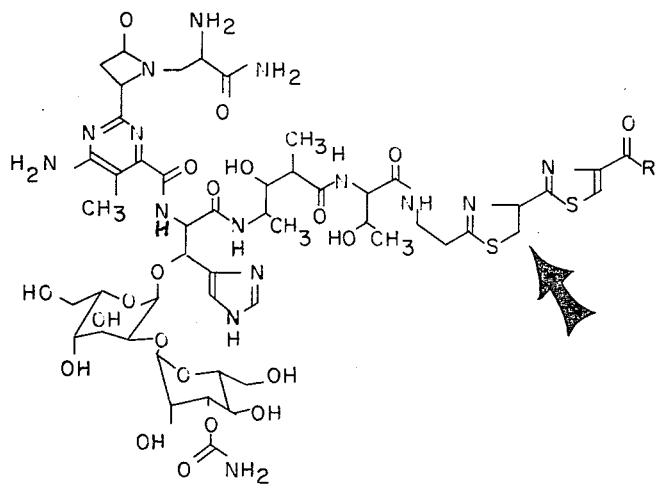
Figure 1:
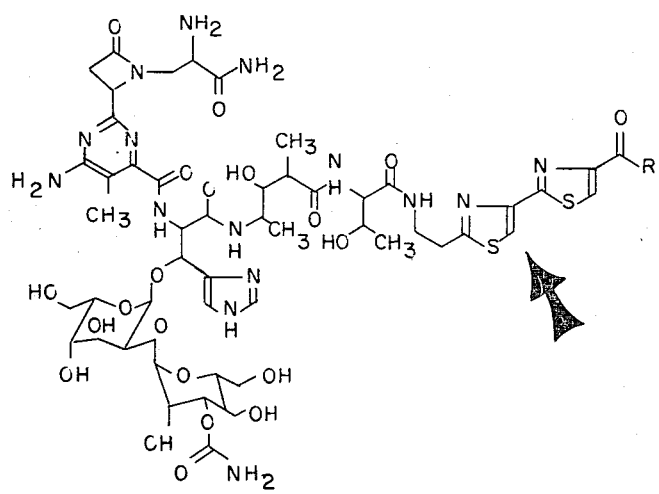

Phleomycin is a mixture of copper-containing glycopeptides with a wide range of antibiotic and antitumour activity. Unfortunately, insufficient selectivity of action—it is nephrotoxic—has inhibited its adoption for clinical use. Copending application No. 84888/75 describes how the problem may be overcome by administering phleomycin in conjunction with certain compounds of the purine series, which, by amplifying its activity, enable useful antibiotic results to be achieved with less than toxic dosage rates. The present application concerns a further but unrelated range of compounds which display phleomycin-amplifying activity. These compounds are active at much lower concentrations than previously known amplifiers (including purines), and therefore there is correspondingly less possibility of side-effects arising from the amplifying compound itself. In this specification references to phleomycin are to be interpreted as applying equally to bleomycin, although, any particular amplifier may not be found to amplify each antibiotic to an equivalent degree. The basic structures of phleomycins and bleomycins are shown in FIG. 1, from which it will be noted that the essential difference between the two types of compounds resides in the presence of two additional hydrogen atoms in the arrowed thiazole ring of phleomycin. Individual phleomycins (and bleomycins) differ from each other structurally only in respect of the terminal group R, which is a substituted amine moiety.

The phleomycin amplifiers according to this invention are characterized as follows:

(i) They comprise two or more six-membered rings, at least one of which is an aromatic hydrocarbon or heterocyclic ring, (ii) They include at least one nitrogen atom, either as a member of a ring or as a member of a ring substituent such as an amino, dialkylamino, trialkylammonio or a dialkylaminoalkylamino group.

(iii) They carry, or readily acquire, one or two positive charges arising from protonation or quaternization of the aforesaid nitrogen atom(s).

(iv) In addition to the substituents referred to in (ii) various other groups may be present, including for example, lower alkyl, lower alkoxy, phenyl, chloro and bromo.

Within the broad scheme outlined above, the amplifiers fall into one or other of the following sub-groups:

Type 1: Derivatives of aromatic ring systems having three or four linearly or angularly annelated (fused) six-membered rings. Up to two carbon atoms in the ring skeleton may be replaced by heteroatoms such as O, N or S.

Type 2: Diarylmethanes, diarylethylenes, diphenyls, diarylamines and azobenzenes, which can adopt spatial conformations corresponding to Type 1 compounds. (In this specification, 'aryl' means having carbocyclic or heterocyclic aromatic ring structure).

Type 3: Triphenylmethane dyes.

Figure 2:
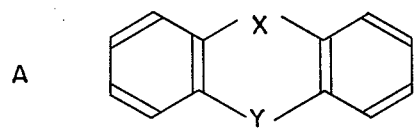
Figure 2:
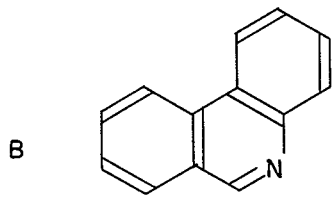
Figure 2:
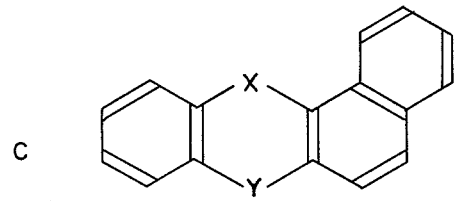
Figure 2:
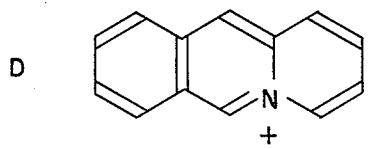
Figure 3:
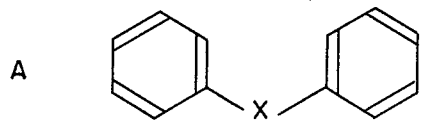
Figure 3:
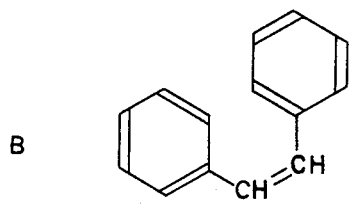
Figure 3:
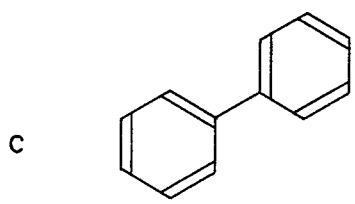
Figure 3:
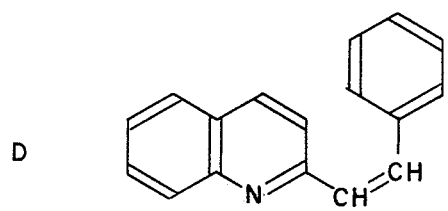
Figure 4:
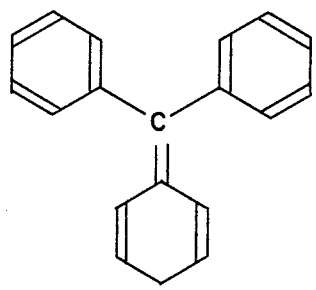

FIGS. 2, 3 and 4 show typical ring skeletons according to the types discussed above. It should be understood that these do not represent individual compounds nor is the list exhaustive; specific compounds are illustrated in Table 1. Although, throughout the specification, charges are indicated as attached to particular atoms, it will be appreciated that in practice the charges are not localized but are associated with the systems as a whole. Similarly the diagrams are to be construed as representing all equivalent resonance structures.

The following examples are illustrative of the efficacy of compounds according to this invention in enhancing the bioactivity of phleomycin and bleomycin:

In vitro

The ability of the compounds to potentiate the cell-killing effects of phleomycin was measured by the following procedure. Stationary phase cultures of *E. coli* B, with or without the compounds under test, were resuspended in growth medium containing phleomycin (2 ug/ml) and incubated at 37° for 30 minutes. The cells were then membrane filtered (0.45 um pore size; 2.5 cms), washed with growth medium (20 ug/ml) and resuspended in growth medium (20 ug/ml) at 37° C. containing various concentrations, between $10^{-10}$ M and $10^{-2}$ M, of the compound under test. As a control, bacteria were exposed to the same range of concentrations of each compound but without the phleomycin pretreatment. To determine viable cell numbers aliquots were taken from each cell suspension after 120 minutes treatment, plated on agar medium and incubated overnight at 37° C. All operations with amplifying agents were carried out in near dark conditions.

The results are set out in Table 1 which shows the concentration of optimum activity of the compounds when used in conjunction with the phleomycin treatment. Compounds were designated as active when the increase in activity with the combined treatment was greater than could be explained by the effects of the two compounds when administered separately.

In vivo

Walker rat carcinoma 256 as the ascites form was passaged in female Sprague Dawley rats. The ascites fluid was aspirated from the peritoneal cavity of animals bearing 6–7 day old tumours and given two minutes treatment in Boyle's solution to remove red cells, the supernatant spun off and the tumour cells suspended in Eagle's Basal Medium to give a final concentration of $10^7$ viable cells per ml. Intraperitoneal injections of 0.1 ml ($10^6$ viable cells) of the suspension were then made into test groups of 6–8 male Srague Dawley rats.

Phleomycin dissolved in phosphate-buffered saline was given to animals in the test groups as 0.1 ml intraperitoneal injections twice daily; each injection was followed by a 0.1 ml intraperitoneal injection of the prospective amplifier. The treatments were given for 5–10 days, at varying concentrations of the phleomycin and amplifier.

The method of evaluating the antitumour effectiveness of the various treatments was based on those used in the screening programme of the Drug Evaluation Branch, National Cancer Institute, National Institute of Health, Bethesda, Maryland, U.S.A. (Cancer Chemotherapy Reports, Vol. 3, No. 2, September 1972). Thus the effectiveness of the drug treatment was measured by the increased survival time, measured in days, of the treated animals over control ones which received no drugs. Dead animals were counted daily, and median survival times (MST) calculated for all groups. Normally, the MSTs for the buffered saline controls were 8–10 days. The ratios (test group median survival time) divided by (control group median survival time)×100 (T/C) were calculated for all the test groups. A T/C value greater or equal to 125 with a test group size of 6 animals was judged significant and the compound was considered active, if the value was repeatable using a different set of animals and sample of tumour.

The results of the experiments are shown in Table 2. From column T/C it will be apparent that an injection rate of 20 ug/kg/day, the phenazine dye Neutral Red was active in that it enhanced the ability of phleomycin at 8, 16 or 32 micrograms/kg/day (MKD) to prolong the survival of rats carrying tumours. Similarly the triphenylmethan dyes, Brilliant Green, Malachite Green and Crystal Violet, as well as the diphenyl methanes Auramin 0, and 4,4'-bis (trimethylamino)diphenylmethane, amplified the antitumour activity of phleomycin.

Phleomycin is known to be taken up by most cellular species and when toxic effects can be avoided it becomes available for treatment of bacterial infections, particularly, by *E. coli* B at a wide range of sites. From present studies it is envisaged that, generally, the administration of phleomycin at a concentration of about 1 mg/l (or mg/kg) in conjunction with one of the amplifying compounds of this invention at a concentration which may be between $10^{-3}$ and $10^{-7}$ molar, depending on the particular compound chosen, should give satisfactory results. For example, a concentration of $10^{-7}$ molar is adequate for Crystal Violet, $10^{-4}$ molar for Ethidium Bromide, and $10^{-3}$ molar for 4,4-bis(-trimethylammonio)diphenylmethane. As with the purine amplifiers described in application No. 84888/75, in some cases optimum results might be obtained by supplying the amplifiers separately and at some time after the phleomycin in order to allow the antibiotic to attach to its target sites in cells.

The cell-killing activity of phleomycin is ascribed to the interference with the ability of cells to replicate, and also to it causing breakage and degradation of the cell DNA. Essentially the level of phleomycin-potentiation displayed by the compounds of this invention is believed to depend on their ability to bind to DNA, as well as to stimulate DNA breakage in response to phleomycin treatment. The binding mechanisms may vary according to the nature of the compound. For instance, cationic molecules possibly bind to the sugar-phosphate DNA back-bone, in some cases binding may involve stacking interactions (intercalation) between the compounds and the parallel-oriented bases of DNA, and sometimes the binding may occur at the outside of the DNA helix. As a rule, it appears that the efficiency of the interaction is connected with base specificity of binding of the amplifier, higher efficiency being correlated with a preference for interaction at adenine-thymine rich regions of DNA.

TABLE 1

Structure and activity of compounds tested for ability to amplify the antibacterial activity of phleomycin

ACRIDINES - FREE BASES

| Compound | $R^3$ | $R^4$ | $R^6$ | Optimum Concentration Tested (M) |
|---|---|---|---|---|
| Acridine | H | H | H | $2.8 \times 10^{-4}$ |
| 3,6-diaminoacridine | $NH_2$ | H | $NH_2$ | $9.5 \times 10^{-5}$ |
| 3-aminoacridine | $NH_2$ | H | H | $1.0 \times 10^{-4}$ |

ACRIDINIUM CHLORIDES

| | $R^2$ | $R^3$ | $R^6$ | $R^9$ | $R^{10}$ | |
|---|---|---|---|---|---|---|
| 3,6-bis(dimethylamino) acridine hydrochloride (Acridine Orange) | H | $N(CH_3)_2$ | $N(CH_3)_2$ | H | H | $1.0 \times 10^{-6}$ |
| 9-aminoacridine hydrochloride | H | H | H | $NH_2$ | H | $2.6 \times 10^{-6}$ |
| 3,6-diamino-N- | | | | | | |

TABLE 1-continued
Structure and activity of compounds tested for ability to amplify the antibacterial activity of phleomycin

| Compound | | | | | | Optimum Concentration Tested (M) |
|---|---|---|---|---|---|---|
| methylacridinium chloride (Acriflavine) | H | NH$_2$ | NH$_2$ | H | CH$_3$ | $3.9 \times 10^{-6}$ |
| Quinacrine | OCH$_2$ | H | Cl | * | H | $3.9 \times 10^{-5}$ |

*R$^9$ = NHCH(CH$_3$) (CH$_2$)$_3$NH(C$_2$H$_5$)Cl$^-$

9,10-DIHYDROANTHRACENES

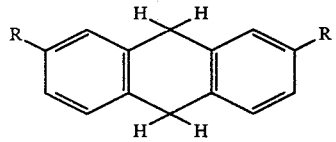

| | |
|---|---|
| 2,7-bis(trimethylammonio)-9,10-dihydroanthracene dichloride: R = N(CH$_3$)$_3$ | $1.4 \times 10^{-6}$ |

9,9'-DIANTHRACENES

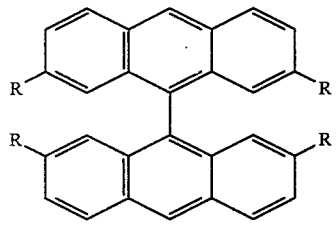

| | |
|---|---|
| 2,2',7,7'-tetrakis(trimethylammonio)-9,9'-dianthracene tetrachloride: R = N(CH$_3$)$_3$ + Cl$^-$ | $5.0 \times 10^{-5}$ |

ANTHRACENES

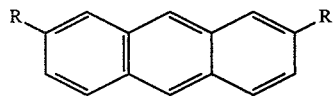

| | |
|---|---|
| 2,7-bis(trimethylammonio)anthracene: R = N(CH$_3$)$_3^+$ Cl$^-$ | $3.0 \times 10^{-4}$ |

PHENANTHRIDINIUM SALTS

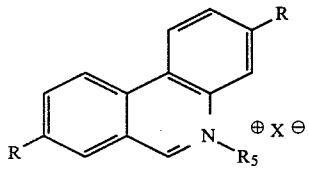

| | R | R$^5$ | R$^6$ | X | |
|---|---|---|---|---|---|
| Ethidium bromide | NH$_2$ | C$_2$H$_5$ | C$_6$H$_5$ | Br | $1.3 \times 10^{-5}$ |
| N-methylphenanthridinium chloride | H | CH$_3$ | H | Cl | $4.0 \times 10^{-6}$ |

PHENAXINIUM CHLORIDES

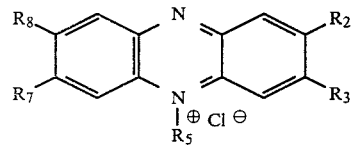

| | R$^2$ | R$^3$ | R$^5$ | R$^7$ | R$^8$ | |
|---|---|---|---|---|---|---|
| N-methylphenazinium chloride | H | H | CH$_3$ | H | H | $3.0 \times 10^{-6}$ |
| Neutral Red | CH$_3$ | NH$_2$ | H | NH$_2$ | H | $3.3 \times 10^{-5}$ |
| Safranin T | CH$_3$ | NH$_2$ | C$_6$H$_5$ | NH$_2$ | CH$_3$ | $1.4 \times 10^{-5}$ |

PHENOXAZINIUM DYES

| | |
|---|---|
| Brilliant Cresol Blue | $3.4 \times 10^{-4}$ |

TABLE 1-continued
Structure and activity of compounds tested for ability to amplify the antibacterial activity of phleomycin

| Compound | Optimum Concentration Tested (M) |
|---|---|
| Nile Blue | $2.7 \times 10^{-6}$ |

PHENAZATHIONIUM DYES

| | $R^7$ | $R^8$ | |
|---|---|---|---|
| Methylene Blue | $N(CH_3)_2$ | H | $1.3 \times 10^{-5}$ |
| Toluidine Blue | $N(CH_3)_2$ | $CH_3$ | $1.6 \times 10^{-5}$ |

XANTHENE DYES

Pyronin Y — $1.7 \times 10^{-4}$

| | R | X | Y | Z | |
|---|---|---|---|---|---|
| Rhodamine G | H | $NH^+$ | $NH(C_2H_5)$ | $C_2H_5$ | $1.2 \times 10^{-4}$ |

PHENOXAZONES 2-aminophenoxazone — $2.5 \times 10^{-5}$

TRIPHENYLMETHANE DYES

| | R | $R_1$ | |
|---|---|---|---|
| Crystal Violet | $N(CH_3)_2$ | $N(CH_3)_2$ | $2.4 \times 10^{-6}$ |

TABLE 1-continued
Structure and activity of compounds tested for ability to amplify the antibacterial activity of phleomycin

| Compound | | | Optimum Concentration Tested (M) |
|---|---|---|---|
| Methyl Violet | $N(CH_3)_2$ | $NHCH_3$ | $1.6 \times 10^{-6}$ |
| Malachite green | $N(CH_3)_2$ | H | $3.0 \times 10^{-6}$ |
| Brilliant Green | $N(C_2H_5)_2$ | H | $9.6 \times 10^{-6}$ |

DIPHENYLMETHANE DERIVATIVES $$R-\phi-\underset{\underset{X}{\|}}{C}-\phi-R$$

| | R | X | |
|---|---|---|---|
| Auramin O | $N(CH_3)_2$ | $NH^+\ Cl^-$ | $3.3 \times 10^{-6}$ |
| 4,4'-bis(trimethylammonio) diphenylmethane | $N(CH_3)_3{}^+\ Cl^-$ | $H_2$ | $2.9 \times 10^{-5}$ |

OTHERS

| | |
|---|---|
| phenazine | $2.7 \times 10^{-4}$ |
| benzo (b) quinolizinium chloride | $2.5 \times 10^{-5}$ |
| 4,4'-bis(trimethylammonio)diphenyl-dichloride | $3.1 \times 10^{-4}$ |
| 4-dimethylamino-4'-trimethylammonio stilbene chloride | $3.1 \times 10^{-6}$ |
| 2-p-dimethylaminostyryl-N-ethyl-quinolinium chloride | $3.0 \times 10^{-7}$ |

TABLE 2

| Phleo MKO | Amplifier | Amplifier Dose MKD | Sched. daily | MST | T/C | Group Size |
|---|---|---|---|---|---|---|
| 32 | Neutral Red | 20 | ×2 | >30 | >214** | 8 |
| 32 | — | 0 | ×2 | 11 | 79 | 8 |
| 16 | Neutral Red | 20 | ×2 | >30 | >214** | 8 |
| 16 | — | 0 | ×2 | 10 | 71 | 8 |
| 8 | Neutral Red | 20 | ×2 | 20 | 143** | 8 |
| 8 | — | 0 | ×2 | 14.5 | 103 | 8 |
| 0 | Neutral Red | 20 | ×2 | 11.0 | 79 | 8 |
| 0 | Buffer Saline Control | 0 | ×2 | 14 | (100) | 8 |
| 20 | Brilliant Green | 640 | ×2 | 11 | 138** | 7 |
| 20 | — | 0 | ×2 | 9 | 112 | 7 |
| 0 | Brilliant Green | 640 | ×2 | 9 | 112 | 7 |

TABLE 2-continued

| Phleo MKO | Amplifier | Amplifier Dose MKD | Sched. daily | MST | T/C | Group Size |
|---|---|---|---|---|---|---|
| 10 | Brilliant Green | 640 | ×2 | 11 | 138** | 7 |
| 10 | — | 0 | ×2 | 8 | 100 | 7 |
| 5 | Brilliant Green | 640 | ×2 | 10 | 125** | 7 |
| 5 | — | 0 | ×2 | 8 | 100 | 7 |
| 0 | Buffer Saline Control | 0 | ×2 | 8 | (100) | 35 |
| 8 | Malachite Green | 52 | ×2 | 16.5 | 206** | 6 |
| 8 | — | 0 | ×2 | 8.5 | 107 | 6 |
| 0 | Malachite Green | 52 | ×2 | 8 | 100 | 6 |
| 0 | Buffer Saline Control | 0 | ×2 | 8 | 100 | 30 |
| 4 | Crystal Violet | 0.5 | ×2* | >30 | 250** | 8 |
| 4 | — | 0 | ×2* | 13 | 108 | 8 |
| 0 | Crystal Violet | 0.5 | ×2* | 12.5 | 104 | 8 |
| 0 | Buffer Saline Control | 0 | ×2* | 12.0 | (100) | 8 |
| | *twice daily from days 2 to 10 | | | | | |
| 8 | Auramin 0 | 7.6 | ×2 | 18 | >180** | 6 |
| 8 | — | 0 | ×2 | 9.5 | 95 | 6 |
| 0 | Auramin 0 | 7.6 | ×2 | 9.5 | 95 | 6 |
| 0 | Buffer Saline Control | 0 | ×2 | 10.0 | (100) | 30 |
| 4 | 4,4′-bis(trimethylammonio) diphenylmethane dichloride | 270 | ×2 | 10.0 | 125** | 8 |
| 4 | — | 0 | ×2 | 8.0 | 100 | 8 |
| 0 | 4,4′-bis(trimethylammonio) diphenylmethane dichloride | 270 | ×2 | 8.0 | 100 | 8 |
| 0 | Buffer Saline Control | 0 | ×2 | 8.0 | (100) | 32 |

Explanatory Notes:
MK = micrograms/kilogram
MKD = micrograms/kilogram animal weight/day
MST = median survival time in days
T/C = Ratio of survival in treatment group / survival in control group
**125 for a group size of 6 animals is taken as positive

We claim:

1. A method for potentiating the antibiotic activity of phleomycin or bleomycin which comprises administering phleomycin, bleomycin or mixtures thereof in association with a compound having a basic ring structure selected from the group consisting of:

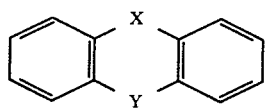

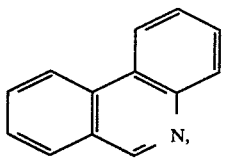

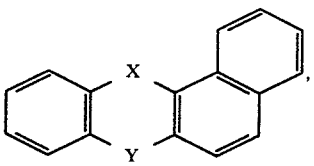

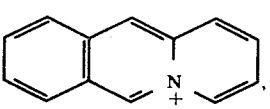

Wherein
X is CH; CH$_2$; N; NH; O; S
Y is CH; CH$_2$; N; O; S,

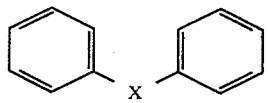

Wherein X is CH, CH$_2$, N or NH,

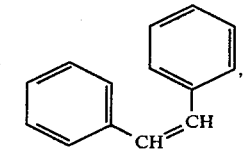

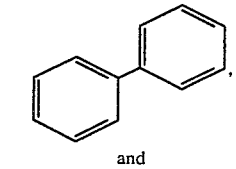

and

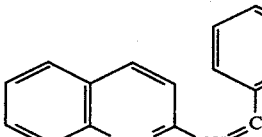

said compound including at least one nitrogen atom, either as a member of a heterocyclic ring or as a member of a ring substituent, said substituent being selected from the group consisting of amino, dialkylamino, trialkylamino and dialkylamino alkylamino, and carrying, or being capable of readily acquiring, one or two positive charges as a result of protonation or quaternization of said at least one nitrogen atom.

2. The method of claim 1 wherein said compound is a diarylmethane, diarylethylene, diphenyl, diarylamine or azobenzene which is able to adopt a spatial configuration corresponding to the aromatic ring systems defined in claim 1.

3. A pharmaceutical composition comprising a member selected from the group consisting of phleomycin, bleomycin or mixtures thereof and an antibiotic activity potentiating amount of a compound having a basic ring structure selected from the group consisting of:

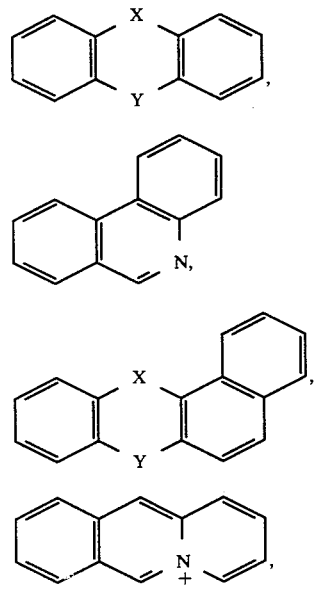

wherein
X is CH; CH$_2$; N; NH; O; S
Y is CH; CH$_2$; N; O; S,

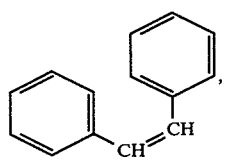

wherein X is CH, CH$_2$, N or NH,

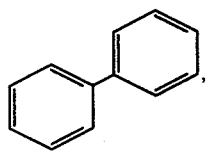

and

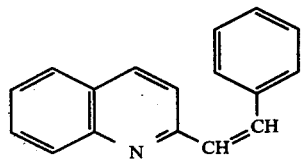

said compound including at least one nitrogen atom, either as a member of a heterocyclic ring or as a member of a ring substituent, said substituent being selected from the group consisting of amino, dialkylamino, trialkylamino and dialkylamino alkylamino, and carrying, or being capable of readily acquiring, one or two positive charges as a result of protonation or quaternization of said at least one nitrogen atom.

4. The method of claim 1 wherein the potentiating agent is

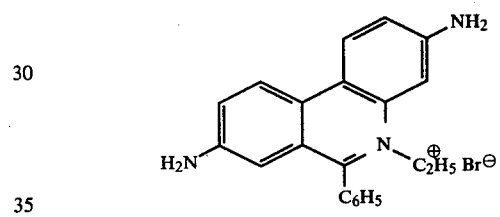

5. The method of claim 1 wherein the potentiating agent is

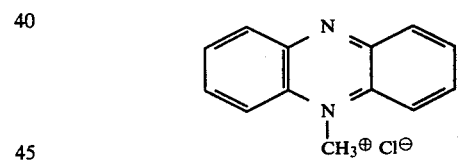

6. The method of claim 1 wherein the potentiating agent is

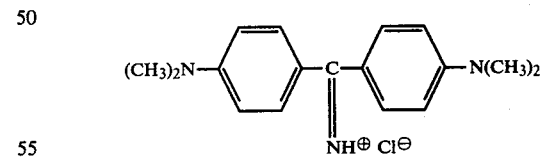

7. A method according to claim 1, wherein the potentiating compound is 4,4'-bis(trimethylammonio)diphenylmethane.

* * * * *